United States Patent [19]

Eldredge

[11] Patent Number: 4,490,964
[45] Date of Patent: Jan. 1, 1985

[54] GRAIN LOSS INDICATOR

[76] Inventor: Kim W. Eldredge, Blyth Rd., Clare, State of South Australia, Australia

[21] Appl. No.: 146,364

[22] Filed: May 2, 1980

Related U.S. Application Data

[63] Continuation of Ser. No. 926,157, Jul. 19, 1978, abandoned.

[30] Foreign Application Priority Data

Aug. 17, 1977 [AU] Australia .............................. PD1276

[51] Int. Cl.³ ...................... A01D 41/00; A01D 45/00
[52] U.S. Cl. ................................ 56/10.2; 56/DIG. 15
[58] Field of Search ....................... 56/10.2, DIG. 15; 130/27 R, 24

[56] References Cited

U.S. PATENT DOCUMENTS

| | | | |
|---|---|---|---|
| 3,593,720 | 7/1971 | Botterill et al. | 56/DIG. 15 |
| 3,606,745 | 9/1971 | Girodat | 56/DIG. 15 |
| 3,610,252 | 10/1971 | De Coene et al. | 56/DIG. 15 |
| 3,805,798 | 4/1974 | Girodat | 56/10.2 |
| 3,935,866 | 2/1976 | Northrup et al. | 56/DIG. 15 |
| 3,939,846 | 2/1976 | Drozhehan et al. | 56/DIG. 15 |
| 4,004,289 | 1/1977 | Kirk | 56/DIG. 15 |

FOREIGN PATENT DOCUMENTS

| | | | |
|---|---|---|---|
| 2448745 | 4/1976 | Fed. Rep. of Germany | 56/DIG. 15 |
| 1157337 | 7/1969 | United Kingdom | 130/27 R |

*Primary Examiner*—Paul J. Hirsch
*Attorney, Agent, or Firm*—Norbert P. Holler

[57] ABSTRACT

Sensor member having on it a ceramic crystal, is secured to a sieve or sieve frame of a combine harvester to be shaken with the sieve or sieve frame being so located that any grain which is discharged from the sieve and otherwise wasted will impact upon the sensor and cause an electrical signal to be transmitted by the crystal, the signal being amplified and transmitted to a readout station which enables the operator to immediately identify when grain is wasted. In being shaken along with the sieve the sensor presents a clean face to the grain, which might otherwise be partly obscured by chaff or other discrete material and this results in a higher degree of accuracy in the determination of wasted grain.

8 Claims, 6 Drawing Figures

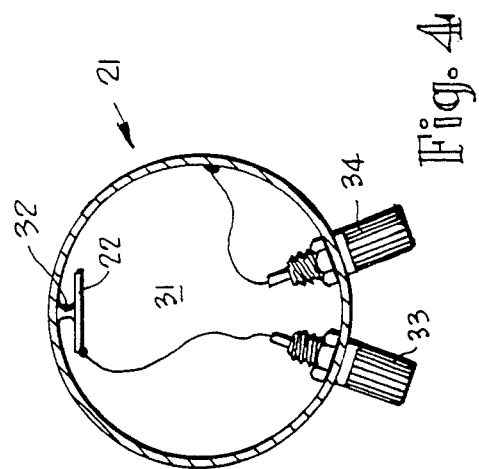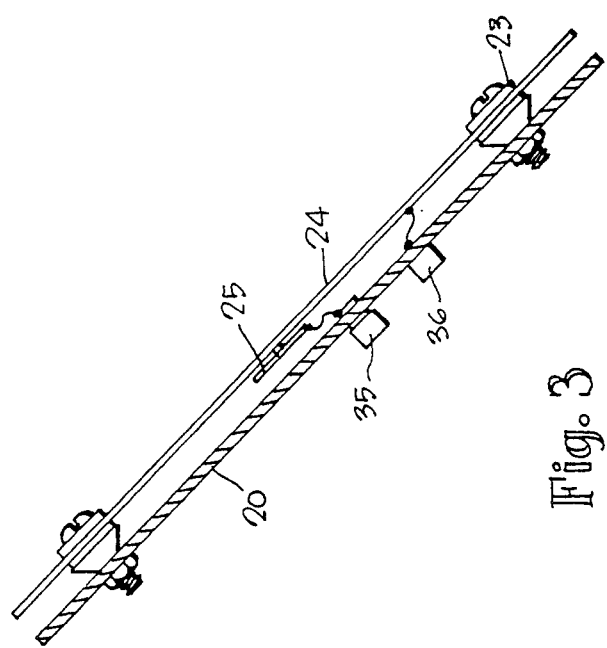

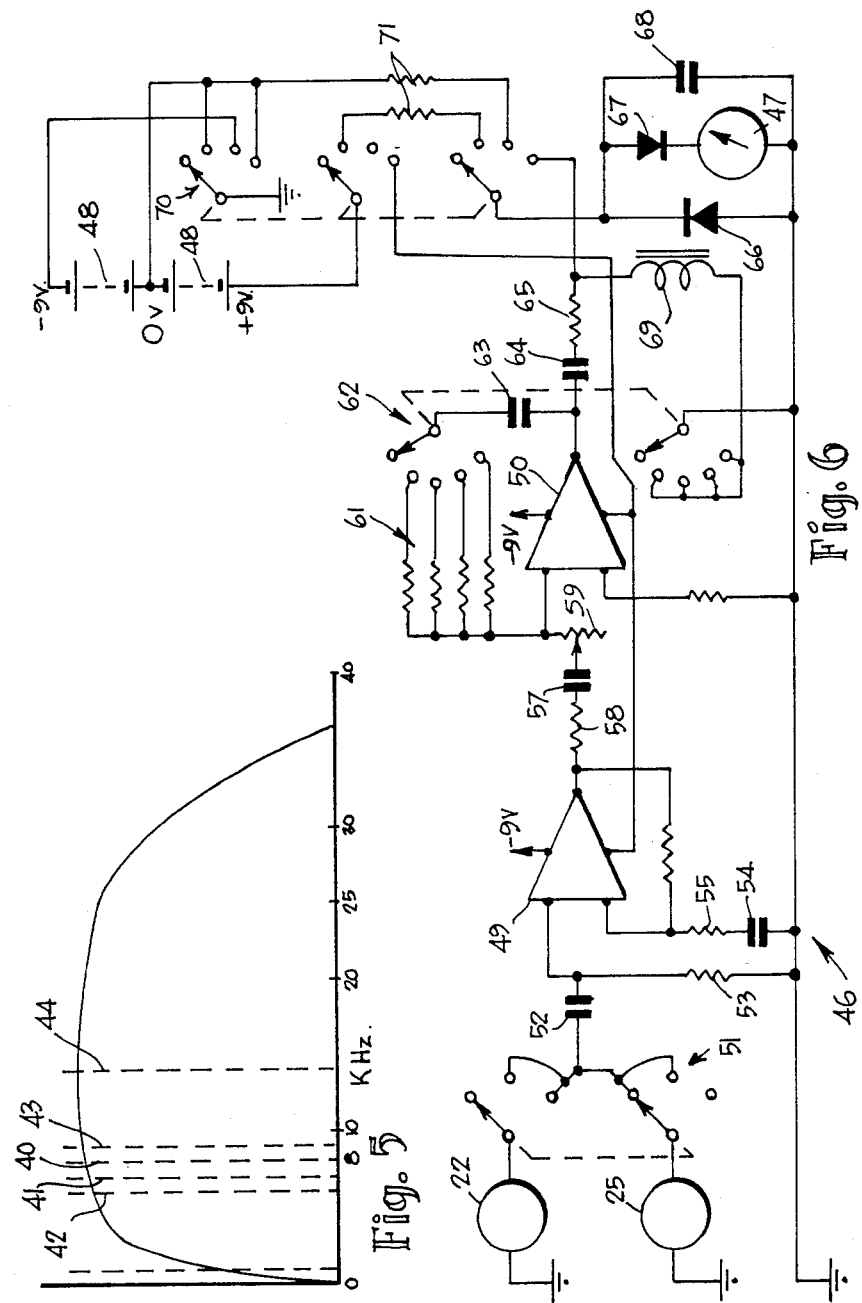

GRAIN LOSS INDICATOR

This is a continuation of application Ser. No. 926,157, filed July 19, 1978, abandoned.

This invention relates to an indicator which is useful for indicating the grain loss from a combine harvester.

BACKGROUND OF THE INVENTION

Because of wide variations which occur in crops which are harvested, a need has been recognised for an indicator which will indicate the grain loss.

When a crop is harvested, the stalk and heads are cut off at about mid length, and fed into a thresher. The husks are blown out by a fan situated beneath the thresher. If there is too much draft the fan will cause excessive quantities of grain to be blown out with the husks. Straw is also thrown onto the straw walkers of the combine, and the straw walkers carry the straw to the back of the machine and on the ground. If there is too much intake by the machine for the capacity of the thresher, the thresher becomes overloaded and does not fully thresh all the heads of the stalks, and this also leads to grain loss along with the straw as it is discharged from the walkers.

This problem has been recognised, and in the U.S. Pat. No. 3,593,720 to J. R. Botterill and U.S. Pat. No. 3,606,745 to J. C. F. Girodat, grain loss monitors were disclosed which were arranged to detect the number of grain kernels passing per unit of time at the discharge end of the walker or the sieves. There have been developments on these early Patents, and in the U.S. Pat. No. 3,939,846 to Drozhzhin et al. there was described a device which included a transducer for measuring the amount of grain lost by the thresher and a transducer for measuring the amount of grain supplied to the hopper, the outputs of the transducers being connected to a ratio detector. In the device of Kirk, U.S. Pat. No. 4,004,289 there was described a device wherein chaff impinged upon a sensor to provide a signal which passed through two or more band pass filters centred at predetermined frequencies. In the U.S. Pat. No. 3,935,866 et al, (assigned to Allis-Chalmers Corporation) there was described a device wherein a monitor derived a grain loss rate signal which was in accordance with the number of grains impinging on a transducer, and this was related to a ground speed signal to provide a reading of percent grain loss per acre.

With all the prior art specified above, and otherwise known to the Applicant, there has been a basic problem which has not been overcome heretofore. Under main circumstances of use, the grain impinging on the sensor is associated with relatively large quantities of chaff or straw, and accurate readings of loss are difficult to achieve. The main object of this invention therefore is to provide a simple grain loss indicator wherein the sensor is more sensitive to the grain content of discharged discrete material than has been achieved heretofore.

SUMMARY OF THE INVENTION

Briefly in this invention, there is provided a sensor member which is arranged to be shaken as discrete material is discharged over it. By this means, there is little or no build up of chaff or other discrete material, and consequently a clean sensor face is presented to the discrete material (including the discharged grain kernels) as the discrete material passes over the sensor.

More specifically, in one aspect this invention consists of a grain loss indicator for indicating grain loss from a combine having harvesting means, thresher means, straw walkers, sieves, means to impart fore-and-aft movement to the straw walkers, and means impart shaking movement to the sieves, comprising:

a sensor member, means securing the sensor member with respect to at least one of the sieves so as to also be subject to said shaking sieve movement, said sensor member being located rearwardly of the sieves and across the path of flow of discrete material as it is discharged over the sieves, an impact detecting transducer carried by and secured with respect to said sensor, electrical readout means, and an electrical signal amplifier electrically interconnecting said transducer and readout means.

Sensor materials which have been used heretofore have frequently employed plastics having a piezo-electric crystal embedded therein or secured thereto. However, I have found that by the use of sheet metal it is possible to have a relatively wide sensor which can extend substantially across the whole of the width of the sieves or the walker and that the sensor can provide accurate readings even when large quantities of straw pass over it. Furthermore, some difficulty is normally encountered with prior art devices in achieving a relatively flat response over the frequency range for various grain kernels, and in another aspect of the invention, a piezo-electric crystal is spaced from but secured to the sheet metal with a metal stem. It is found that by so mounting the piezo-electric crystal with respect to the sheet metal, an accurate response can be achieved over a range of frequencies which is much broader than that required to identify the grain kernel impact.

In many combine harvesters there is provided a stiffener plate which extends between the side walls of the harvester, which is disposed rearwardly of the straw walkers and which functions as a chute. In another aspect of this invention, a further sensor is a plate-like member which extends across most or all of the width of the straw walkers to thereby lie across the path of discharge of all or nearly all of the flow of discrete material as it is discharged over the straw walkers, and the plate-like member slopes downwardly in a rearward direction, so that it functions as a deflector plate as well as a sensor. Conveniently, the second sensor can be mounted to the stiffening plate if such exists on the combine harvester to which the device is secured.

BRIEF SUMMARY OF THE SEVERAL VIEWS OF THE DRAWINGS

An embodiment of the invention is described hereunder in some detail with reference to and as illustrated in the accompanying drawings in which:

FIG. 3 is a sectional elevation illustrating the mounting of the second sensor on a plate which extends between the side plates of a combine harvester rearwardly of the straw walkers, FIG. 4 is a section through the first sensor, showing the mounting of the piezo-electric crystal, FIG. 5 is a graph which illustrates the frequency imparted to the sensor by various grain kernels, and FIG. 6 is a circuit diagram of the amplifier which interconnects the impact detecting transducer and the readout meter.

DETAILED DESCRIPTION OF THE DRAWINGS

Figure 1:
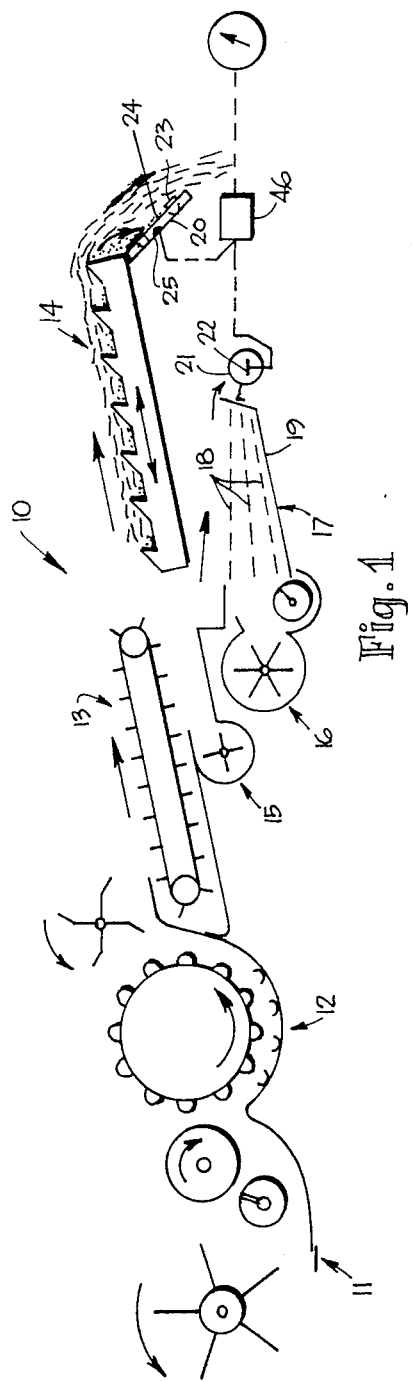
FIG. 1 is a diagrammatic sectional elevation of a combine harvester, illustrating a first sensor at the discharge end of the sieves, and a second sensor at the discharge end of the straw walker.

Referring first to FIG. 1, a combine harvester 10 comprises a cutter knife 11 which severs a crop approximately mid way up its stalk, the severed crop being fed into a thresher 12 and transported by a conveyor 13 to a straw walker 14. A first fan 15 blows a draught of air below the straw walker, and a second fan 16 blows a second draught of air through a sieve 17 which comprises three sieves plates 18 carried on a frame 19, the frame 19 being provided with means to cause it to shake. The straw walker 14 is also provided with means to cause it to move in a fore-and-aft direction. At the rear end of the straw walker 14 there is provided a stiffener plate 20. Mounted on the aft end and rearwardly of the sieve frame 19 is a first sensor 21 containing a piezo-electric transducer 22, and mounted on the stiffener plate 20 by means of rubber grommets 23 is a second sensor plate 24 having on it a second piezo-electric transducer 25. Except for the sensors and transducers, the combine harvester 10 is one well known in the art, but the invention is equally applicable to other combine harvesters of different construction.

Figure 2:
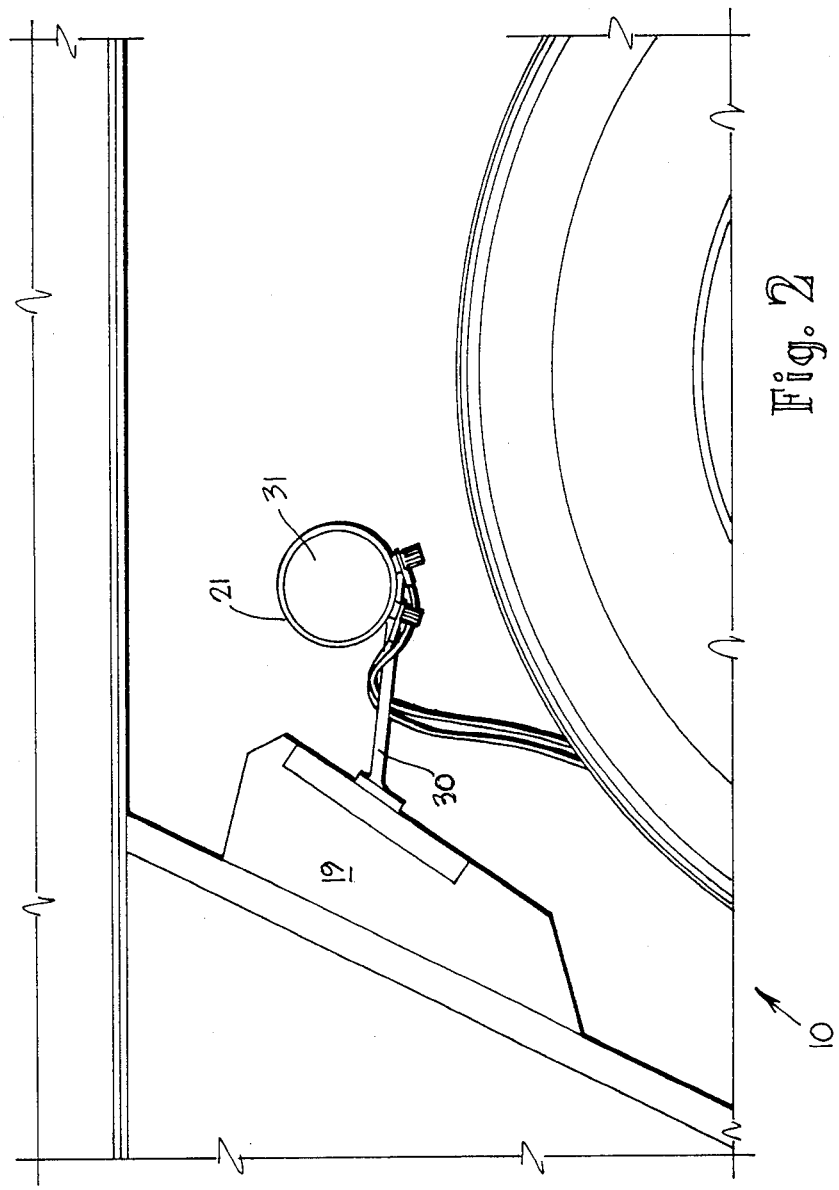
FIG. 2 is a fragmentary perspective view which illustrates the mounting of the first sensor or the sieve frame.

As shown best in FIG. 2, the sieve frame 19 has secured to it brackets 30 and these brackets 30 support the first sensor 21 which comprises a tubular member formed from sheet metal and having closed ends 31, the sensor containing a piezo-electric crystal 22 secured within it and separated from the sheet metal of the sensor by a stem 32 which is of substantially smaller size than the crystal. The crystal 22 is wired to a terminal 33, and the sheet metal of the first sensor 21 to a second terminal 34, which is merely an earth terminal.

As shown in FIG. 3, the stiffener plate 20 has secured to it a second sensor plate 24 by means of the rubber grommets 23, and the second sensor plate 24 carries on it the piezo-electric transducer 25. The transducer 25 is wired to a terminal 35, and the sheet metal of the plate 24 to a terminal 36. The angle of inclination of the second sensor plate is a little less than the angle of inclination of straw being discharged, and the straw is arranged to be deflected only over the lower (downstream) end of the sensor plate, the plate being of such an extent that its upper end region is, as a consequence, free to feel the impact of grain kernels released from the straw as it leaves the straw walkers under all conditions of straw discharge.

In both instances, the piezo-electric transducer is a 40 KHz ceramic crystal manufactured by T.D.K. Electronics of Tokyo, Japan. It is a crystal of the type used for ultrasonic transducers. This is found to provide about the required frequency for a relatively flat response curve (FIG. 5) between about 1 and 20 KHz.

Both the first sensor 21 (the tubular sieve sensor) and the second sensor 24 (the deflector plate straw walker sensor) extend for substantially the full width of respectively the sieves and the straw walkers, and in both instances they are arranged in the path of flow of discrete material discharged respectively from the sieve and straw walker. The precise positioning can best be determined empirically, and will slightly vary with different combine harvesters. However, the first sensor 21 in being continually shaken along with the sieve frame, will always present a relatively clean surface to the grain kernels which impact against it, and it is found that this provides a very accurate reading, and when combined with the sheet metal of the sensor and the stem 32 which connects the sheet metal to the transducer 22, substantial avoidance of errors of reading is achieved.

FIG. 5 illustrates the approximate frequencies which are imparted to various grains. In FIG. 5, the abscissa is indicative of frequency and is marked in KHz while the ordinate is indicative of signal strength when different frequencies are imparted to the sheet metal of the respective sensors. The dotted line designated 40 at 8 KHz indicates the approximate frequency imparted by the wheat kernels impacting against the sensor surface. Similarly, the line 41 designates barley, the line 42 designates oats, the line 43 designates rice and the line 44 designates lucerne (alfalfa)

Reference is now made to the circuit diagram of FIG. 6. The circuit is essentially an amplifier generally designated 46 and this interconnects the two transducers 22 and 25 to an output reading meter 47. Power is derived from batteries 48, there being two 9 volt packs, one supplying 9 volt negative to earth and the other 9 volt positive to earth for two amplifiers, designated respectively 49 and 50, each amplifier being a standard SN741 amplifier which is readily available from any one of a number of manufacturers.

Three wires, that is from the sieve transducer 22, the walker transducer 25, and common earth are plugged into the back of the amplifier circuit. A three position two gang rotary switch 51 selects the input to the circuit, by switching in singly the "sieves" transducer or "walkers" transducer, or putting them both in parallel for the intermediate position shown. The impedance of the transducer crystals is very high and the frequency required to be amplified lies between 1 and 25 HKz. The low frequency vibration of the machine, between 50 and 100 Hz is not required.

The input from the transducers into the first amplifier 49 passes through a 0.47 microfarad capacitor 52 and a 1 megohm resistor 53 extends between the output side of capacitor 52 and earth, to match roughly the crystal impedance. The first amplifier 49 is a simple non-inverting amplifier with a gain of 10. This has a high frequency rolloff of approximately 60 KHz. This high frequency is susceptible to high frequency interference, and a small capacitor 54, in series with resistor 55, reduces the frequency rolloff to approximately 25 KHz, and makes the gain of amplifier 49 frequency dependent. The output of the first amplifier 49 passes through a large coupling capacitor 57 and a resistor 58 into the potentiometer 59 which constitutes a sensitivity control. The capacitor 57 is utilised to prevent a build-up of direct current output from the amplifier 49.

From the sensitivity control potentiometer 59, the signal is fed into the second stage inverting amplifier 50, again a SN741 amplifier. A bank of resistors 61 of differing values provides a range of feedback and therefore a range of amplifier gain. The resistors 61 are selected by a wiper arm of a two gang five position switch 62, and the feed back loop incorporates a capacitor 63 to eliminate direct current gain. The open position on the switch 62 is a readout check position for checking the needle deflection of the readout meter 47, and since there is no resistor in the feedback loop there is infinite gain. This functions to reveal whether or not the sensors are operating by picking up any movement of any sort of the sensor. The five position switch also disconnects a low frequency filter choke described hereunder.

The output from the inverting amplifier 50 passes through a large coupling capacitor 64 and resistor 65, this increasing the time constant through the meter so as to damp needle movement. The signal is then passed through the metering circuit which incorporates the diode rectifiers 66 and 67, and a capacitor 68 is placed across this circuit for smoothing purposes.

A 2.5 mH choke 69 bridges the output at the locality of resistor 65 to earth, and therefore filters out machine vibration of 100 Hz and less. This circuit is broken however when the switch 62 is in the position shown, which is the meter check position.

The switch 70 is a three gang four position switch, which as illustrated can switch in the two 9 volt packs separately, through respective resistors 71, providing means whereby the cell level can be double-checked at any time.

A consideration of the above embodiment will reveal that the invention provides a number of advantages over prior art. Firstly, the first sensor secured to the sieve frame is always kept clean and is responsive to grain impact under severe conditions. Secondly, the flat deflector plate sensor at the discharge end of the walkers is effective because of its size and inclination, and because the discrete material discharged by the walkers must flow over it. The electrical circuit will be seen to provide means for checking sensors at all times, through the switch 62, and finally, as illustrated best in FIG. 5, the circuit of FIG. 6 provides a broad range of control, using only simple amplification techniques. Only very high and very low frequencies are shunted in this circuit.

It will be understood that the foregoing description of preferred embodiments of the present invention is for purposes of illustration only, and that the various structural and operational features herein disclosed are susceptible to a number of modifications and changes none of which entails any departure from the spirit and scope of the present invention as defined in the hereto appended claims.

What is claimed is:

1. Grain loss indicator for indicating grain loss from a combine having harvesting means, thresher means, straw walkers, sieves, means to impart fore-and-aft movement to the straw walkers, and means to impart shaking movement to the sieves, comprising:
    a sensor, means securing the sensor with respect to at least one of the sieves so as to also be subject to said shaking sieve movement, said sensor being located rearwardly of the sieves and extending across substantially the full width of the sieves so as to lie across substantially the entire path of flow of discrete material that has not passed through the sieves and is discharged over the sieves, and the portion of said sensor that is positioned to be impacted by the said discrete material being a sheet metal member,
    an impact detecting transducer carried by and secured to said sensor, said transducer comprising a piezo-electric crystal, and a metal stem interconnecting said crystal to said sheet metal member, the stem being of substantially smaller size than the crystal and spacing the latter a sufficient distance from said sheet metal member to enable an accurate response to be achieved over a range of frequencies broader than that required to identify the different types of grain kernels that may impact against said sheet metal member,
    electrical readout means, and
    an electrical signal amplifier electrically interconnecting said transducer and said readout means.

2. Grain loss indicator according to claim 1, wherein said sheet metal member is a tube having an interior wall surface, and said stem interconnects said crystal to the interior wall surface of the tube.

3. Grain loss indicator according to claim 1, comprising a further sensor positioned rearwardly of the straw walkers, and a further impact detecting transducer carried by and secured to said further sensor, said further sensor extending across substantially the full width of the straw walkers so as to lie across substantially the entire path of flow of additional discrete material that is discharged over the rear ends of the straw walkers, and the portion of said further sensor that is positioned to be impacted by the additional discrete material being a plate-like member made of sheet metal and mounted so as to slope downwardly in a rearward direction with respect to the straw walkers.

4. Grain loss indicator for indicating grain loss from a combine having harvesting means, thresher means, straw walkers, sieves, means to impart fore-and-aft movement to the straw walkers, and shaking means to impart shaking movement to the sieves, comprising:
    a first sensor located rearwardly of the sieves and extending across substantially the full width of the sieves so as to lie across substantially the entire path of flow of discrete material that has not passed through the sieves and is discharged over the rear ends of the sieves, and means connecting said first sensor to said shaking means so as to effect shaking movement of said first sensor when the sieves are shaken,
    a second sensor located rearwardly of the straw walkers and extending across substantially the full width of the straw walkers so as to lie across substantially the entire path of flow of additional discrete material that is discharged over the rear ends of the straw walkers, the portion of each said sensor that is positioned to be impacted by the associated discrete material being a member made of sheet metal, a piezo-electric crystal for each sensor, and a metal stem interconnecting the sheet metal member of each sensor to its respective crystal so as to enable each crystal to be responsive to impact vibrations imparted to its associated sheet metal member, each stem being of substantially smaller size than its associated crystal and spacing the crystal a sufficient distance from the respective sheet metal member to enable an accurate response to be achieved over a range of frequenices broader than that required to identify the types of grain kernels that mau impact against said sheet metal members,
    a signal readout meter, an amplifier circuit interconnecting the piezo-electric crystals and the readout meter, and high and low frequency filters in the amplifier circuit effective to remove signals above 25 KHz and below 100 Hz.

5. Grain loss indicator according to claim 4, wherein in said amplifier circuit comprises two amplifiers in tandem, and a sensitivity control variable resistor is interposed between the output of the first said amplifier and the input of the second said amplifier.

6. Grain loss indicator according to claim 4, wherein the second said amplifier comprises a bank of feedback resistors of differing values which provide a range of amplifier gain, and a multi-position switch selectivity placing said feedback resistors into circuit, said multi-position switch having an open circuit position at which said second amplifier has infinite gain, thereby constituting readout check means.

7. Grain loss indicator according to claim 4, wherein the sheet metal member of said second sensor is a plate arranged at a rearwardly downward angle of inclination to the longitudinal extent of the straw walkers which is less than the angle of inclination of the downward path of flow of said additional discrete material when the same is discharged from the straw walkers, the angle of inclination and the width of said plate being of sufficient magnitudes to ensure that the straw component of said additional discrete material will be deflected by the lowermost rear end region of said plate and that at least a part of said plate upwardly of said rear end region thereof will remain sufficiently clear of straw under all conditions of discrete material discharge to enable said plate to be responsive to impact of grain kernels released from the straw as said additional discrete material is discharged from the straw walkers.

8. Grain loss indicator according to claim 4, wherein the sheet metal member of said first sensor is a tube having an interior wall surface, and said stem interconnects the associated crystal to the interior wall surface of the tube.

* * * * *